United States Patent [19]

Gönner

[11] Patent Number: 4,874,250
[45] Date of Patent: Oct. 17, 1989

[54] APPARATUS FOR EXAMINATION OF HEATS OF TRANSFORMATION OF MATERIAL SAMPLES

[75] Inventor: Winfried Gönner, Überlingen, Fed. Rep. of Germany

[73] Assignee: The Perkin-Elmer Corporation, Norwalk, Conn.

[21] Appl. No.: 942,934

[22] Filed: Dec. 4, 1986

Related U.S. Application Data

[63] Continuation of Ser. No. 604,780, Apr. 27, 1984, abandoned.

[30] Foreign Application Priority Data

May 28, 1983 [DE] Fed. Rep. of Germany ....... 3319410

[51] Int. Cl.[4] ..................... G01N 25/20; G01N 25/00
[52] U.S. Cl. ........................................ 374/43; 374/31; 374/10; 374/12; 422/63
[58] Field of Search ................ 374/10, 12, 31, 33, 374/43; 422/51, 63, 64, 67, 65; 414/198, 223; 324/308, 433

[56] References Cited

U.S. PATENT DOCUMENTS

| | | | |
|---|---|---|---|
| 2,707,356 | 5/1955 | Bayha | 324/73 AT |
| 4,151,252 | 4/1979 | Marchand et al. | 422/51 |
| 4,178,800 | 12/1979 | Thomann | 374/33 |
| 4,317,360 | 3/1982 | Vasilenko et al. | 374/12 |
| 4,368,991 | 1/1983 | Hentze | 374/12 |
| 4,447,395 | 5/1984 | Englar | 422/63 |

FOREIGN PATENT DOCUMENTS

| | | | |
|---|---|---|---|
| 2358088 | 5/1975 | Fed. Rep. of Germany | 414/223 |
| 0022495 | 3/1978 | Japan | 374/31 |

*Primary Examiner*—Charles Frankfort
*Assistant Examiner*—Thomas B. Will
*Attorney, Agent, or Firm*—Francis L. Masselle; Ronald G. Cummings; Edwin T. Grimes

[57] ABSTRACT

The automatic serial testing of the heats of transformation of material samples is accomplished. The samples are enclosed in capsules which are placed into sample carriers on a turntable. A transfer mechanism transfers the capsules from the turntable to a controllably heatable test sample receiver and, after the measurement, back to the turntable. The entire arrangement is located in a housing filled with nitrogen. The sample carriers with the capsules can be inserted into this housing and onto the turntable through an air lock.

13 Claims, 5 Drawing Sheets

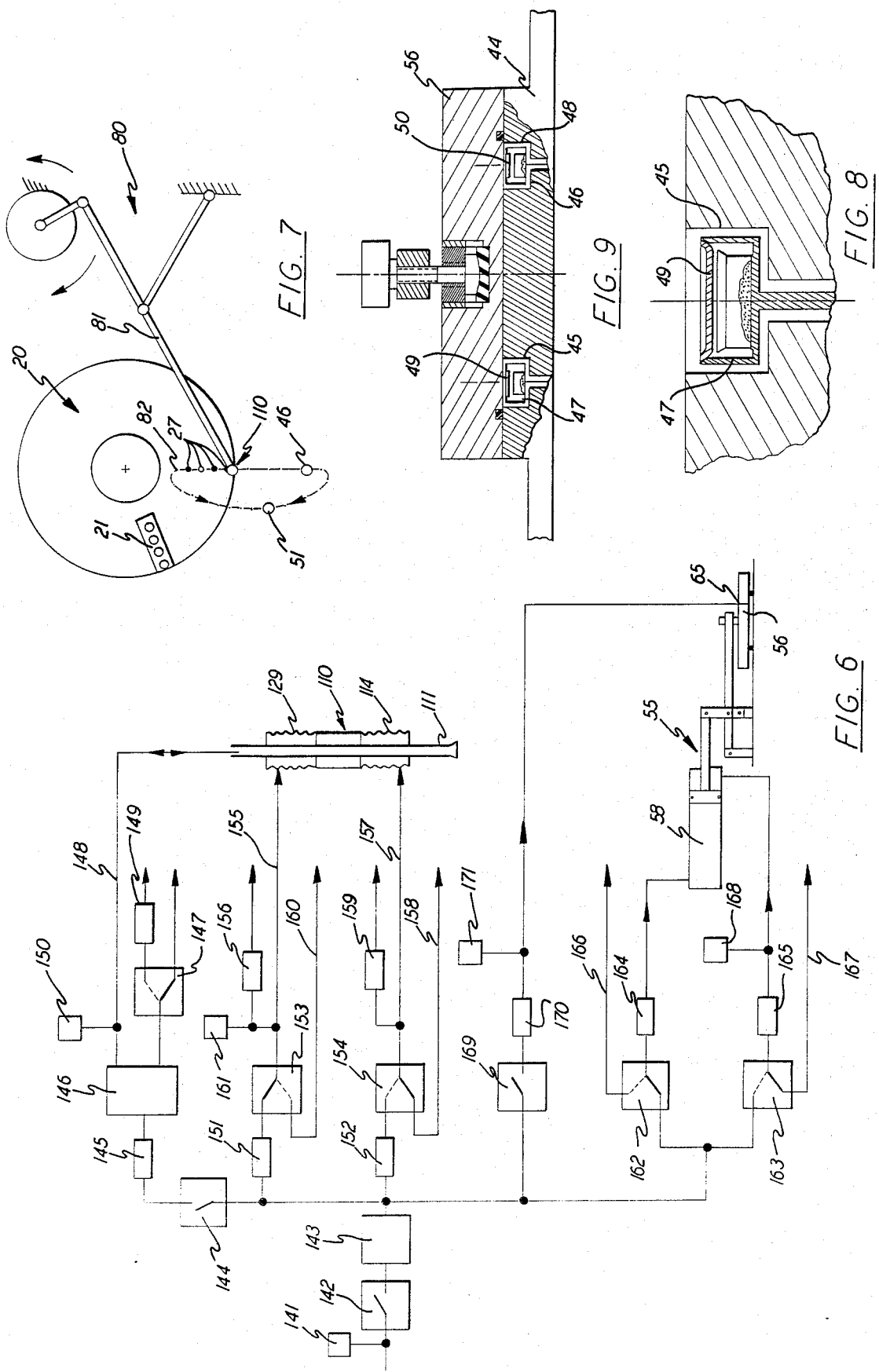

APPARATUS FOR EXAMINATION OF HEATS OF TRANSFORMATION OF MATERIAL SAMPLES

This is a continuation of application Ser. No. 06/604,780 filed Apr. 27, 1984 now abandoned.

BACKGROUND OF THE INVENTION

The present invention relates generally to an apparatus for the examination of the heats of transformation of material samples and, in particular, relates to such an apparatus having a test sample receiver for a test sample, a reference sample receiver for a reference sample, means for cooling or heating both the test and reference samples and a measuring device which responds to differences in the heating up characteristic of the test and reference samples.

M. L. Clarebrough et al., in "The Determination of the Energy Stored in a Metal During Plastic Deformation" (Proc. of The Royal Society, 1952, Vol. A 215, pp. 507–524), describe a device for continuous and measurable variation of the temperature of a test sample and a reference sample. In that device respective heating elements serve to heat the test sample and the reference sample. These heating elements are arranged in heater circuits with a part common to both heating elements. A control loop, including sensors for measuring the temperature difference between the test and reference samples, adjusts this temperature difference to zero by varying the energy supply to the heating element associated with the test sample. Thereby the difference of the energy supplied to the test and the reference samples, which energy is measured with a highly precise differential wattmeter, provides a measure of the heats of transformation.

Another apparatus of the present type is illustrated and described in German Auslegeschrift 1 473 303. Therein small heating plates for accommodating a test and a reference sample are arranged side by side and spaced from each other in a housing.

The known apparatus permits only individual measurements with which the test and reference samples are inserted by hand into the apparatus.

SUMMARY OF THE INVENTION

Accordingly, it is one object of the present invention to provide an apparatus which permits the examination of a plurality of test samples sequentially and automatically.

This object is achieved, at least in part, by an apparatus including a test sample store which permits a plurality of test samples enclosed in capsules to be inserted into a program-controlled transfer mechanism by means of which a test sample can be transferred from the test sample store into the test sample receiver and removed therefrom. A program control device is arranged to control the cooling or heating device (hereinafter sometimes referred to as "the temperature control means or device") and the transfer mechanism so that during a measuring cycle, a test sample is sequentially transferred from the test sample store into the test sample receiver by the transfer mechanism; heating or cooling of the test and reference samples is effected by the temperature control means to carry out the measurement and the test sample is removed from the test sample receiver by the transfer mechanism.

The entire apparatus is isolated from the environment by a housing to eliminate external influences and is charged with the samples through a lock.

The samples are enclosed in discoid capsules and disposed in groups of four, in complementary-shaped recesses of a right rectangular prism-shaped sample carrier. This sample carrier is longitudinally translated through the lock onto a turntable having corresponding recesses extending radially inwards and is held there by magnets. For further charging with sample carriers the turntable is advanced by the angle of rotation determined by the number of the recesses so that the next recess is aligned with the opening of the lock. When the turntable is fully loading, a predetermined number of four-sample capsules is located on the turntable, each with its long axis disosed radially.

A circular heating plate with two discoid recesses is located beside the turntable, the two recesses being diametrically opposed on a straight line through the central points of the turntable and the heating plate and equally spaced from the central point of the heating plate. One of the recesses accommodates the reference sample in a small heatable reference sample receiver and the other recess accommodates the sample capsule to be analyzed in a similar test sample receiver.

When a test sample capsule is deposited, the test sample receiver is covered by a small individual platinum cover, while the entire heating plate for the heating process is covered by a cover plate which, attached to a lever arm, is rotated onto the heating plate by a pneumatic cylinder. In order to change the sample the individual platinum cover is removed and desposited on a post or column.

A four-membered lever transmission is dimensioned with respect to its structure-fixed points and the lengths of the members so that a point of a connecting link or coupler follows a straight-line motion on a patch congruent with the straight line between the central points of the turntable and of the heating plate so that, with appropriate positioning of the turntable, the four sample capsules on the side of the turntable facing the heating plate and the two test and reference sample receivers have their respective centers on a straight-line underlying the straight line part of the coupler point travel. The column with the platinum cover is centrally covered by the arcuate segment of the coupler curve.

At the point of the connecting link, a sample capsule pick-up mechanism is arranged vertically with respect to the plane of motion the lever transmission. On this lifting pick-up mechanism a suction head can be raised and lowered by means of a pneumatic system. The suction head member itself is formed like a suction cup at its end facing the sample capsules in order that a sample capsule, after the suction tip of the pick-up member has been lowered down on it, can be safely attached by suction and held by means of vacuum.

Thus the complete feed procedure takes place as follows: the turntable is charged with the sample carriers through the lock. One sample carrier at a time is centrally aligned to the straight-line part of the coupler point travel path of the crank transmission by means of a control device. The lifting mechanism, being located in the initial position in an upper end position, is moved along the coupler curve to the position of the first sample capsule, lowered down thereon and attached to the capsule by vacuum. Then the suction member, with the capsule attached is picked up and moved on the position of the test sample receiver on the heating plate. There the suction member is lowered down and the sample capsule separated from the suction member by a pressure pulse, and the suction member is lifted again. The coupler with the lifting mechanism is now moved to the position overlying the column with the platinum cover. The suction member is lowered down thereon attaches it by suction and is lifted. The lifting mechanism is moved back on the position of the sample, lowered down and releases the platinum cover by means of a pressure pulse. Then the lifting mechanism lifts anew the suction member and is moved out of the swivelling area of the cover plate of the heating plate to the initial position, whereupon the cover plate is swung on the heating plate, and the sample capsule and the reference sample are heated or cooled, respectively. When the corresponding measurements are completed the cover plate opens. The lifting mechanism is moved to the sample position on the heating plate, first takes up the platinum cover and deposits it on the column, then returns to the sample position, picks up the sample capsule and transports it back to the sample receiver on the turntable. There the sample is deposited and the lifting mechanism is moved back to its initial position. When the cycle is repeated the lifting mechanism approaches the position of the second sample and proceeds as described above. The test samples can be chosen freely by means of an operator device. When the desired number of capsules of a carrier is worked off, the turntable is rotated and the next sample carrier is positioned.

Other objects and advantages will become apparent to one skilled in this art from the following detailed description read in conjunction with the appended claims and the drawings attached hereto.

BRIEF DESCRIPTION OF THE DRAWING

An apparatus, embodying the principles of the present invention is described in greater detail hereinafter with reference to the accompanying drawing, not drawn to scale, wherein:

FIG. 6 shows the pneumatic diagram for the sample pick-up mechanism and the cover mechanism of the heating plate;

FIG. 7 is an illustration of the principle of the transfer mechanism through a crank transmission with an appropriate coupler curve;

FIG. 8 shows a test or reference sample receiver at an enlarged scale; and

FIG. 9 shows a section of the heating plate with cover plate and test and reference sample receiver.

DETAILED DESCRIPTION OF THE INVENTION

Figure 1:
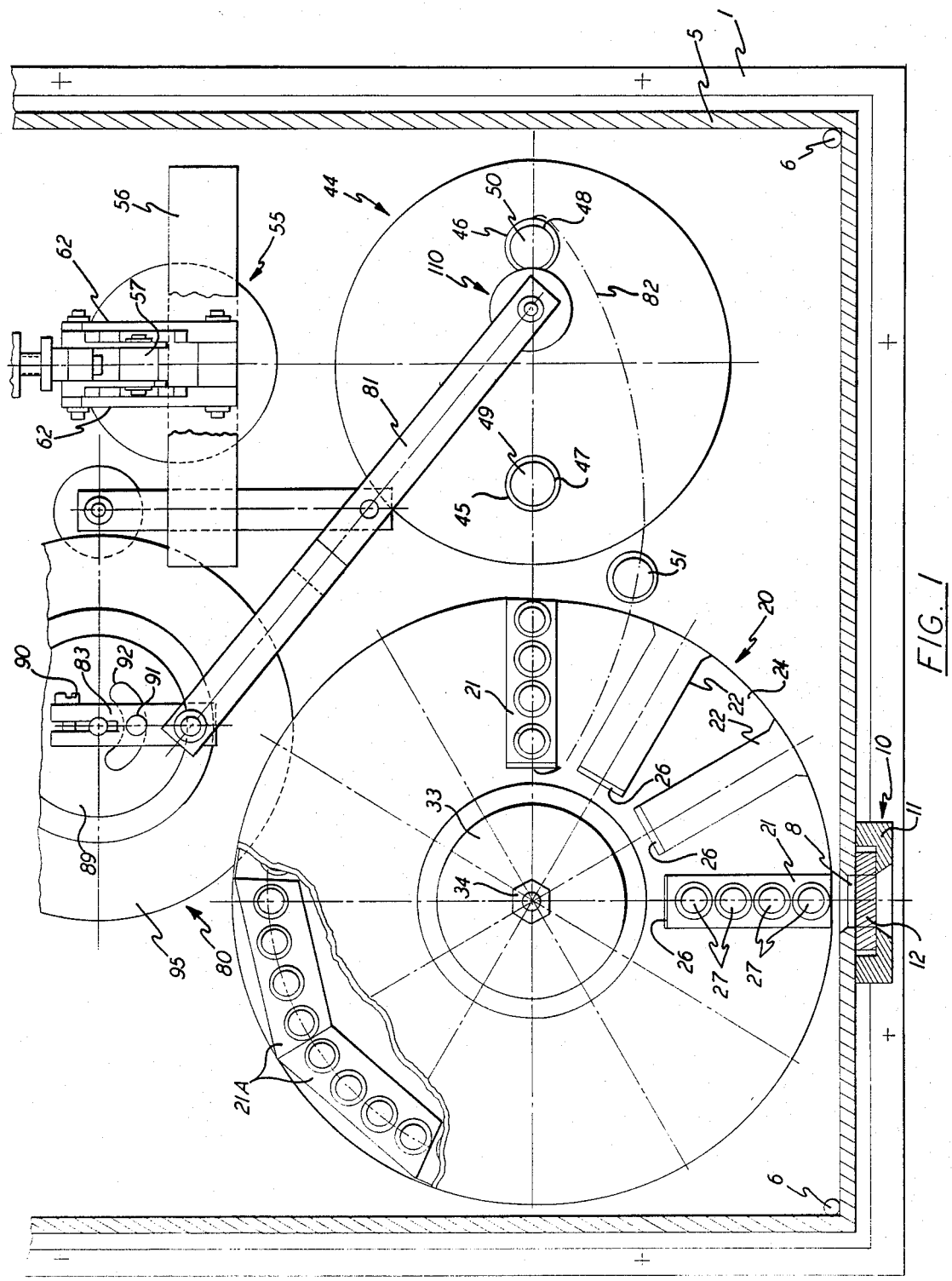
FIG. 1 shows, in a section through the housing, a plan view of the transfer mechanism, the heating plate and its cover mechanism.
Figure 2:
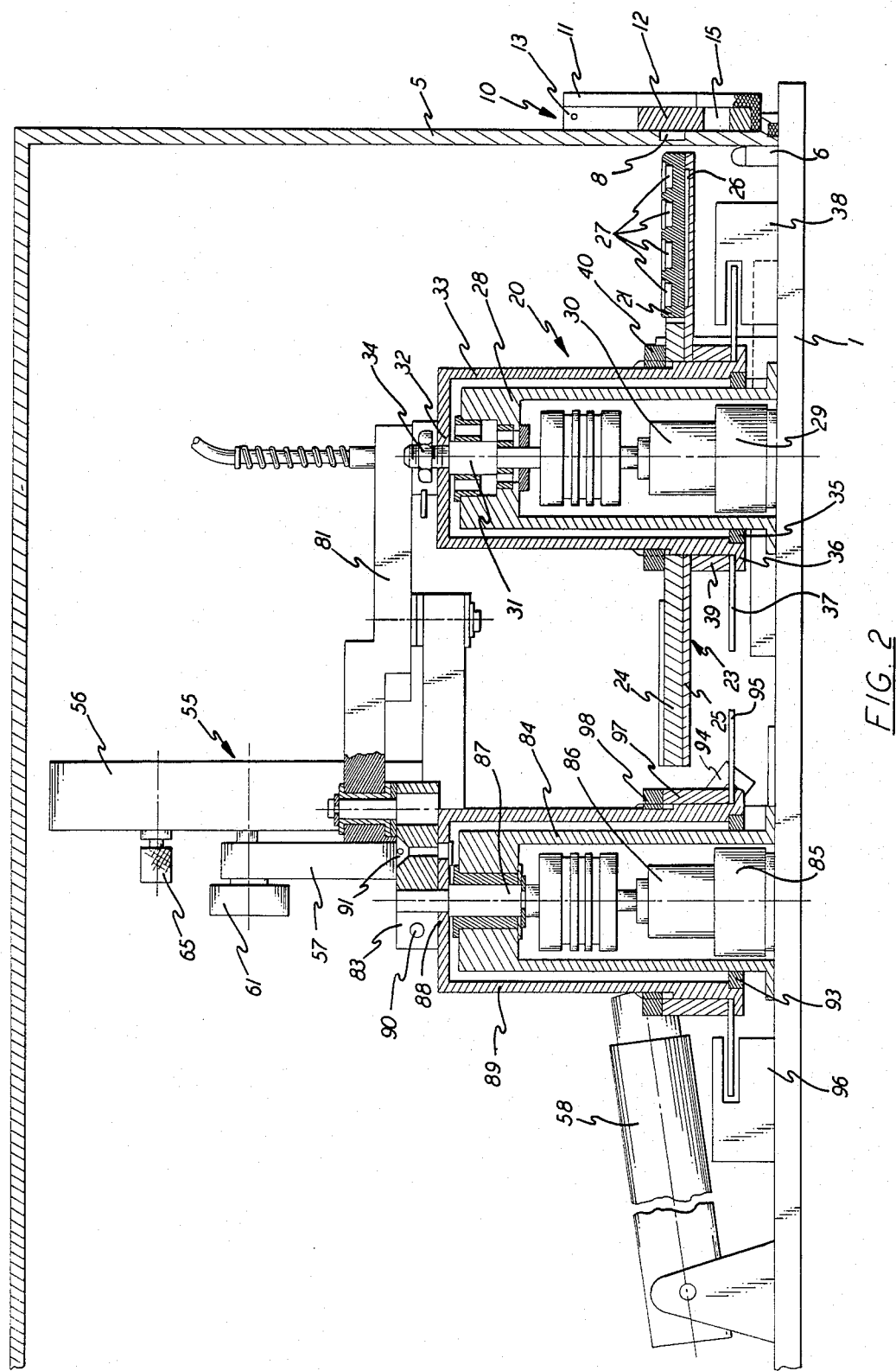
FIG. 2 shows, with reference to FIG. 1, the left side view of the entire apparatus with sections through the housing, the turntable and the drive of the lever transmission.
Figure 3:
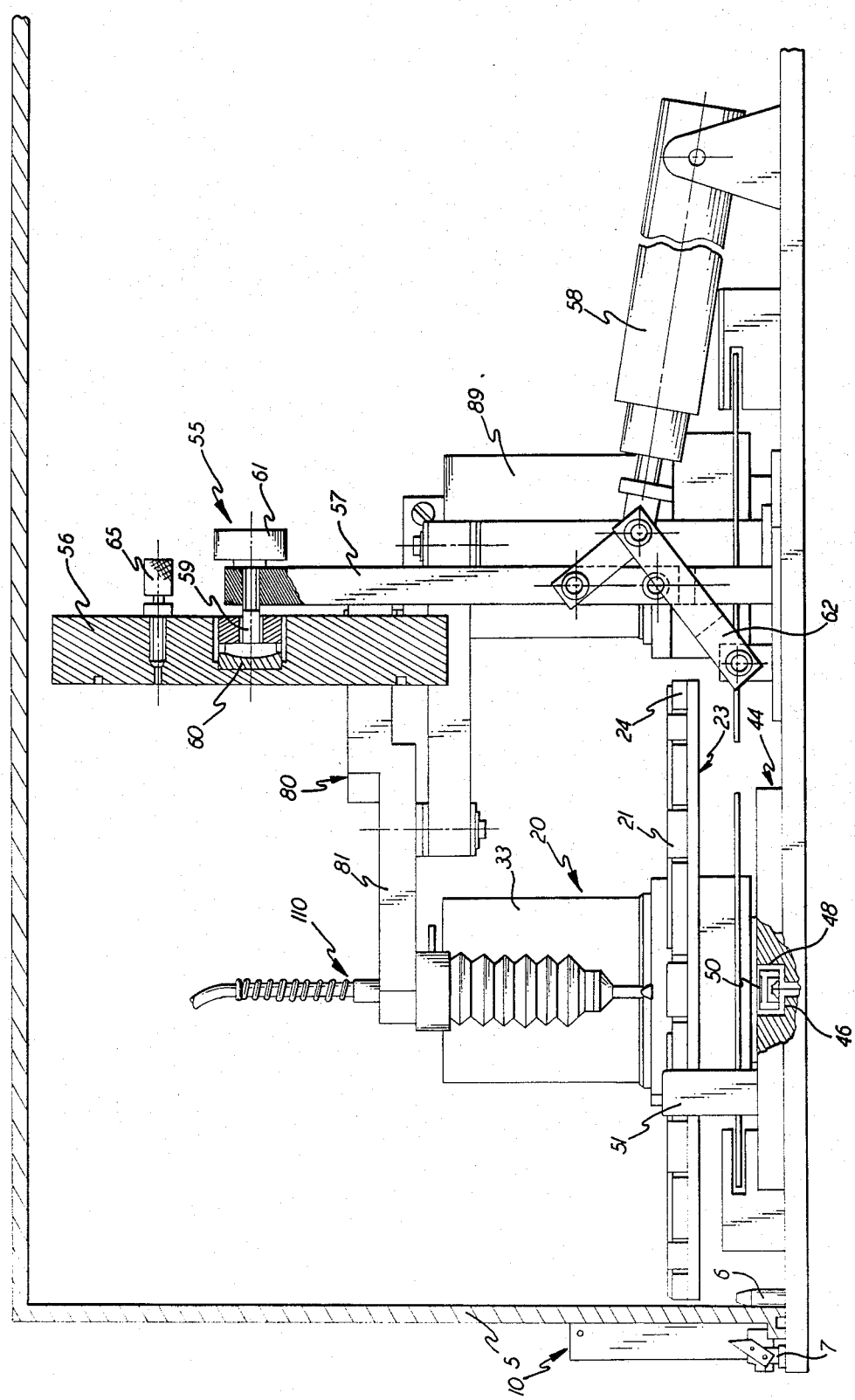
FIG. 3 shows, with reference to FIG. 1, the right side view of the entire apparatus with sections through the housing and the cover plate of the heating plate.

In FIGS. 1, 2 and 3, three views of the individual units of the feed and measuring device are illustrated in their spatial relative arrangement. A housing, generally indicated at 5 in these Figures, includes a lock 10 through which sample carriers 21 are passed into the interior of the apparatus. The housing 5 is positioned relative to a base plate 1 by pins 6 and is secured in position by quick-locks 7 (FIG. 3).

Figure 5:
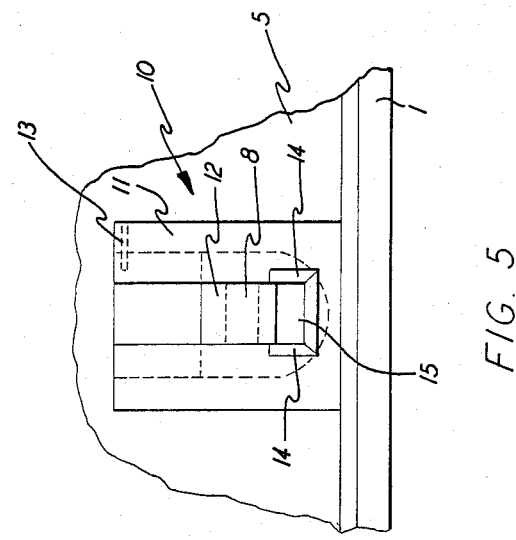
FIG. 5 shows a plan view of a lock for sample charging.

The lock 10 is more fully illustrated in FIG. 5 as a section in the plan view and includes a guiding part 11 slotted outwards, which has a U-shaped cutout 9 in the wall of the housing 5 for accommodation of a slide 12. The upward movement of the slide 12 is limited by a pin 13. Preferably, the sample carriers 21 are elongated right rectangular prism-shaped units, along which a number of circular recesses 27 provided with a bezel are formed for reception therein of flat, cylindrical (discoid) sample capsules. In the embodiment described hereinafter each sample carrier 21 is deemed, by way of example to include four sample capsules therein.

When a sample carrier 21 passes through the lock 10, its front end is inserted into an opening 15 of the slide 12 which is in its lower position as illustrated in FIGS. 2 and 5. The opening 15 corresponds to the crosssection of the sample carrier 21. The sample carrier 21 is supported by inclined guiding surfaces 14 of the guiding part 11. Thereafter, the sample carrier 21 together with slide 12 is lifted so that the opening 15, with the front end of the sample carrier 21, is aligned with a corresponding rectangular opening 8 in the housing 5. The sample carrier 21 can now be entirely pushed through, whereupon the lock 10 is closed again by the slide 12 sliding down after the end of the sample carrier 21 has passed the opening 15 of the slide 12.

In the interior of the housing 5 the sample carriers 21 slide in radially extending, rectangular recesses 22 of a sample table 23 of a turntable unit 20. The sample table 23 includes two discs 24 and 25 made of nonmagnetizable material and provided with the radial recesses 22 which correspond to the base area dimensions of the sample carrier 21. The disc 25 has radial recesses, corresponding to the number of recesses 22 in the disc 24, in which recesses magnets 26 are retained for holding the sample carriers 21, which are made of magnetizable material, on the sample table 23.

A stepping motor 29, having gearing 30, is disposed in a bell-shaped housing 28 which is connected to the base plate 1. A shaft 31, having a shoulder 32, is secured in conventional manner against axial displacement and extends out of the bell-shaped housing 28 at the upper side thereof. The shaft 31 is connected to the motor 29 via a friction clutch and the gearing 30. A second bell-shaped housing 33 is supported on the shoulder 32. This housing 33 is axially and radially non-slidingly connected on the shaft 31 by, for example, a screw-thread 34. The second bell-shaped housing 33 is angularly freely movable relative to the base platefixed bell-shaped housing 28. A sliding bearing 35, for example one formed from polytetrafluoroethelene (PTFE), is provided between the two housings and also acts as a seal to prevent contaminants from entering into the shaft bearings in the housing 28. The housing 33 is also provided with a shoulder 36 at its bell-shapedly opened, lower end, on which shoulder 36 a circular code disc 37 is provided with a bore corresponding to the diameter of the housing 33 at this place and is supported thereby. The code disc 37 carries the markings relevant for the positioning of the sample table 23 relatively to a lever transmission 80 and to the lock 10 and is read by means of a sensor 38. A spacer ring 39 is supported on the code disc 37, and a sample table 23 is supported thereon. The sample table 23 includes the two discs 24, 25 adapted to each other with respect to the angle of rotation. By means of the spacer ring 39 the position of the sample table 23 may be adjusted to the level of the position of the opening 8 in the housing so that the sample carriers 21 can be pushed through the lock 10 onto the sample table 23 without level offset. The code disc 37 and the sample table 23 are axially and angularly non-slidingly connected to the housing 33 by, for example, a knurled nut 40. The turntable unit 20 may be adjusted to the other units by adjusting the code disc 37 relative to the sample table 23 via the nut 40. The motor 29 may be adjusted relative to the code disc 37 and the sample table by means of the screwthread 34.

A modification of the shape of the sample carriers 21 and of the arrangement on the sample carrier 23 is indicated in FIG. 1 by the broken line illustration of the turntable 20 with the shape modification 21A of the sample carriers.

A heating plate 44 is located on the base plate 1 beside the turntable unit 20. Two recesses 45 and 46 are disposed on the heating plate 44 diametrically opposite each other at equal distances from the central point of the heating plate 44. FIGS. 8 and 9 show, on an enlarged scale, the test sample receiver 47 and the reference sample receiver 48, each of which is formed by a cup-shaped, heatable portion, which portions being arranged in the recesses, 45 and 46, respectively, and spaced from the walls thereof. The test sample receiver 47 and the reference sample receiver 48 each accommodate a capsule with a material sample to be examined (test sample) and a reference sample respectively.

The capsules have, as can be seen best from FIG. 8, a pot-shaped lower portion, the rim of which extends conically outwards. A cup-shaped closing portion with a correspondingly conical rim, bent off upwards is placed on the pot-shaped lower portion, the rims placed one upon the other being cold welded. Thus, cup-shaped recesses having rims extending essentially conically outwards are formed on the upper side of the capsules. These rims form a guide for a pneumatic lifting mechanism described hereinafter. The test sample receiver 47 and the reference sample receiver 48 are each covered by a platinum cover, 49 and 50, respectively. The platinum cover 50 on the recess 46 for the reference sample remains in place, while the cover 49 over the measuring head of the sample recess 45 is deposited on a column 51, while the sample is being changed. The platinum covers, 49 and 50 are also cup-shaped on the upper side with inclined rims for guiding the lifting mechanism.

During the heating process the heating plate 44 is covered by a cover deployment mechanism 55. To this end a cover plate 56, attached to an extended rocker 57 of a four-membered crank transmission, is swung on to the heating plate 44 by a pneumatic cylinder 58. As best appears in FIG. 3 cover plate 56 is resiliently connected to the rocker 57 though a fungiform bolt 59 and a concave rubber cup 60 or cup springs in order to compensate for small angle inaccuracies and to ensure that the cover plate 56 is deposited to make completely planar contact on the heating plate 44. Larger angle inaccuracies between hinged down cover plate 56 and the heating plate 44 may be adjusted via the screwing of the bolt 59 in the rocker 57 after a locking jam nut 61 has been released. Preferably, the angle of motion of the rocker 57 between open and closed positions of the cover plate is 90°. By appropiate choice of the dimensions of the four-membered crank transmission, the crank end point of which is engaged by the pneumatic cylinder 58 a smaller angle than the 90° of the rocker is swept over by the crank 62 for the opening and closing of the heating plate cover, whereby a better dynamic system behavior is obtained.

The sample capsule is transported from its position in the recesses of the sample carriers 21 on the sample table 23 of the turntable unit 20 to the test sample receiver 47 on the heating plate 44, by a lifting mechanism 110. The lifting mechanism 110 is attached to the extended coupler 81 of a lever transmission 80. The dimensions of the lever transmission 80 are chosen such that part of the coupler curve 82 of the point corresponding to the fastening point of the lifting mechanism 110 on the coupler follows a straight-line motion. The three units, turntable unit 20, heating plate 44 and lifting mechanism 80 are so arranged on the base plate that the straight-line part of the coupler curve 82 is congruent with the connecting straight-line through the central points of the heating plate 44 and the turntable unit 20. With corresponding positioning of the sample table 23, the sample recesses 27 of a sample carrier 21 and the recesses, 45 and 46, on the heating plate 44 are located centrally under the straight-line part of the couple curve 82 and thus in the area of translation of the lifting mechanism 110. The length of the straight-line part of the coupler curves is chosen in order that the recesses, 27, 45, 46 are swept over straightly and no interferences occur with the housing 5 or with the housing 33. The column 51, on which platinum cover 50 is deposited while making a sample change is positioned in the arcuate part of the coupler curve 82 between the turntable unit 20 and the heating plate 44. FIG. 7 shows the turntable unit 20, the lever transmission 80 and the relative positions of the lifting mechanism 110 on the coupler curve 82.

A crank 83 of the lever transmission 80 is driven by a driving unit similar to the driving unit of the turntable unit 20. A stepping motor 85 with gearing 86 is disposed in a bell-shaped housing 84 connected to the base plate 1. A shaft 87, secured in a conventional manner against axial displacement, extends out of the bell-shaped housing 84 at the upper side thereof, and is connected to the stepping motor for example, via a friction clutch and the gearing. A second bell-shaped housing 89 is supported on the shoulder 88 on shaft 87.

The crank 83 is axially and radially nonslidingly connected to the shaft 87 via a threaded fastener 90. The housing 89 is axially non-slidingly mounted between the crank 83 and the shaft shoulder 88. Rotation of the housing 89 relative to the crank 83 is prevented by a threaded fastener 91 which permits adjustment of the housing 89 relative to the crank 83 by a circumferential slot 92. The housing 89 is angularly freely movable relative to the base plate-fixed housing 84. A sliding bearing 93, formed from PTFE for example, is provided between the two housings and also acts as a seal to prevent the entry of contaminants in to the shaft bearings in the housing 84. The housing 89 is provided with a shoulder 94 at its bell-shapedly opened, lower end, on which shoulder 94 a circular code disc 95 is supported.

The code disc 95 carries markings for the positioning of the lifting mechanism 110 on the coupler curve and is read through a sensor 96. A spacer ring 97 is supported on the code disc 95. The code disc 95 is axially and radially non-slidingly connected to the housing 89 by a knurled nut 98. To turn the lifting mechanism 110 with respect to the other units the code disc 95 is coarsely adjusted relative to the housing 89 by means of nut 98. The threaded fastener 91 between crank 83 and housing 89 provides means for a finer adjustment.

Figure 4B:
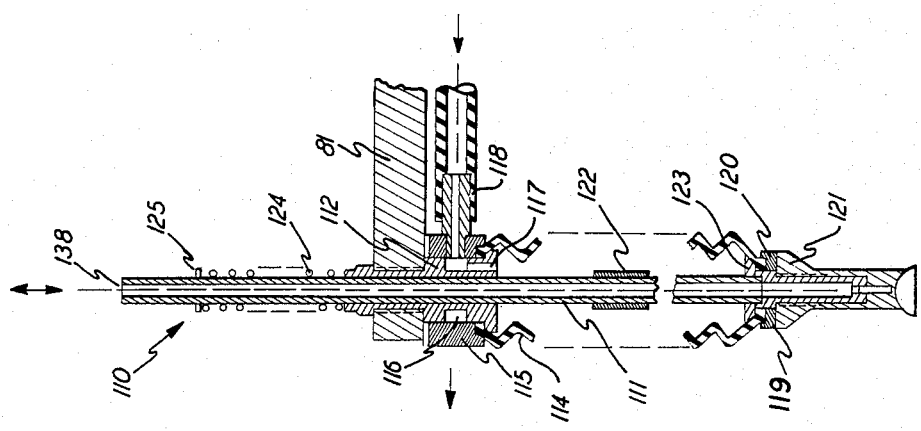
FIGS. 4A and 4B show alternative structural shapes of the sample pick-up mechanism arranged on the coupling link of the crank transmission.
Figure 4A:
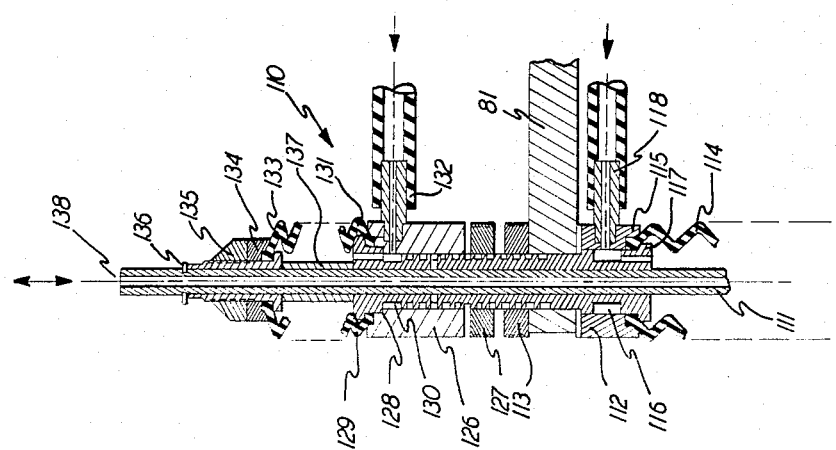

A tubular suction member 111 is raised and lowered by lifting mechanism 110. As shown in FIGS. 4A and 4B this is accomplished either entirely pneumatically or with a combination of a pneumatic system and an oppositely acting spring bias. Tubular suction member 111 is, in both cases, lowered pneumatically. A guide sleeve or bushing 112 is screwed directly (as in FIG. 4B) or by means of a knurled nut 113 (FIG. 4A) to coupler 81. A bellows 114 is clamped between the radially enlarged, lower end of guide sleeve 112 and a ring 115 which is positioned between coupler 81 and the end edge of bellows 114. Guide sleeve 112 is provided with an annular groove 116 from which a bore 117 extends vertically downward to the lower end of the guide sleeve. Ring 115 is provided with a transverse bore into which a hose connection fitting 118 is threaded or otherwise secured, the inner end opening into groove 116. Bellows 114 at its lower end is clamped between a ring 123, secured by gluing or soldering to the lower end of suction tube 111, and a ring 120 urged into clamping coaction with ring 123 by a threaded suction head member 121. A suction tip 119 of neoprene, silicone rubber or the like is disposed at the extreme lower end of member 121 and engages elements to be picked up, e.g, sample capsules and platinum covers. A spacer 122 is freely movable on the suction member 111 and ensures a minimum distance between guiding piece 112 and suction tip 119 for the protection of the bellows 114, when the suction member 111 is moved up. The lower part of the suction tip 119 is enlarged in a nozzle-shaped manner for safely attaching by suction, the capsules and the platinum cover 49 thereto by vacuum.

When the suction tip 119 is lowered, nitrogen under pressure is blown through the hose socket 118 into the groove 116 and therefrom through the bore 117 into the bellows 114. The pressure acts on the annular surface 123 and moves the suction member 111 and the suction tip 119 downwards. When no more nitrogen is blown through the socket 118, the suction member 111 in the embodiment of the lifting mechanism 110 in FIG. 4B is urged upwards by a compression spring 124, which is supported on the guide sleeve 112 and through a spring-abutment ring 125 fixed on the suction member 111, until the spacer 122 engages the guide sleeve 112 and the annular surface 123.

In one modification of the lifting mechanism 110, illustrated in FIG. 4A, the guide sleeve 112 is extended upwardly beyond the coupler 81. At the upper end thereof a section of tube 126 is screwed on and locked by a knurled jam nut 127. In the free upper portion of tube section 126 a second guide sleeve 128 is attached, i.e. screwed in, so that the lower end of an upper bellows 129 is clamped between the radially enlarged upper end of the guide sleeve 128 and the upper end of tube section 126. The guide sleeve 128 is provided with a surrounding groove 130 from which a vertical bore 131 extends upwardly to the upper end of the guiding piece 128. Tube section 126 is provided with a transverse bore and a hose connection fitting 132, the inner opening of which ends in the groove 130. Upper bellows 129 is clamped at its upper end between a clamping piece 133, a ring 134 and a knurled nut 135.

Clamping piece 133 is supported at the upper end on a ring 136 connected to the suction member 111. Analogous to the spacer 122 of FIG. 4B a spacer ring 137 maintains a minimum distance for protection of the bellows.

When now the suction tip 119 in the modification of FIG. 4A is moved upwards, nitrogen or other suitable working gas is exhausted through hose fitting 118 and nitrogen under pressure is applied to the fitting 132. The nitrogen enters the bellows 129 through the groove 130 and the bore 131. The pressure acts on the upper annular surface and moves the suction member 111 upwards.

For attaching by suction and pushing off, respectively, the sample capsule and the platinum cover 49 by the suction tip 119, either nitrogen is taken in through an opening 138 or the capsule and the cover, respectively, is separated from the sucker by a pressure pulse.

FIG. 6 shows the pneumatic diagram for the lifting mechanism 110 and the covering mechanism 55. Nitrogen under pressure passes a pressure sensor 141 and is introduced into the system through a valve 142 and a pressure regulator valve 143. The nitrogen is conducted through a valve 144 into a vacuum generator 146 through a restrictor 145. When the valve 147 is in the lower indexing position, a vacuum is produced in a conduit 148, by means of which the capsules can be attached by suction through the suction member 111. In the upper indexing position of the valve 147, only part of the nitrogen is diverted through a restrictor 149 so that there is an elevated pressure in the conduit 148, by means of which elevated pressure the capsules can be pushed off from the suction member. The pressure conditions are recorded by a pressure sensor 150. Nitrogen under pressure is supplied to valves 153 and 154, through restrictors, 151 and 152. When the valve 153 is in the indexing position "up" and the valve 154 in the indexing position "down", the lifting mechanism is lifted through a conduit 155 and excess nitrogen is vented through a restrictor 156. At the same time, the air volume located in the lower bellows is vented through conduits 157 and 158. When the indexing positions of the valves 153 and 154 are changed, the suction member 111 is lowered through the conduit 157 and excess nitrogen is vented through a restrictor 159. At the same time, the nitrogen volume of the upper bellows 129 is diverted through the conduits 155 and 160. The pressure conditions are detected by a pressure sensor 161. The cover plate 56 is either lifted or lowered by the pneumatic cylinder 58 through valves 162 and 163, depending on the indexing position thereof. The nitrogen flows through restrictors 164, 165 into the cylinder and the outgoing air is diverted through conduits 166 and 167, respectively. A pressure sensor 168 records the pressure conditions. Through a valve 169 and a restrictor 170 it is monitored through the connection tap 65 whether the cover plate is closed and closely engages the heating plate. The feed back is effected through a pressure sensor 171.

The present invention has been described herein via an exemplary embodiment which is not deemed limiting as other configurations and arrangements may also be made which do not depart from the scope of this invention. Consequently, the present invention is deemed limited only by the appended claims and the reasonable interpretation thereof.

What is claimed is:

1. Apparatus for examination of heats of transformation of material samples, comprising:
   a test sample receiver (45) for one of a plurality of individually encapsulated test samples;
   a reference sample receiver (46) for a reference sample;
   a program-controlled cooling or heating device for the controlled cooling or heating of said test and reference samples;
   a measuring device responsive to differences in the heating-up characteristic of said test and reference samples;
   a test sample store for receiving said plurality of individually encapsulated test samples, said test sample store including a turntable adapted to receive elongate sample carriers radially disposed thereon and adapted to contain a plurality of radially-juxtaposed test sample encapsulations;
   a program-controlled transfer mechanism by which one of said plurality of test samples can be transferred from said test sample store into, and removed from, said test sample receiver, said transfer mechanism including
   a lever transmission from which one point in a plane of motion describes a coupler curve passing by said test sample store and said test sample receiver,
   a driving motor for driving said lever transmission, and
   a lifting mechanism movable in a direction normal to said plane of motion for engaging the encapsulation of each said test sample and arranged in said one point of said lever transmission said lever transmission being
   a four-membered lever transmission so dimensioned with respect to its structure-fixed points and the lengths of its members that the coupler curve described by said lifting mechanism extends substantially rectilinearly and radially to said turntable, said lever transmission including
   a first lever connected to a rotatable shaft of said driving motor and extending radially thereto,
   a second lever pivoted in a pivotal point on said first lever and carrying said lifting mechanism, and
   a third lever pivoted at one end of a structure-fixed point and at another end on said second lever between said pivotal point and said lifting mechanism, and
   a program control device for controlling said cooling or heating device and said transfer mechanism whereby during one measurement cycle a test sample is first transferred from said test sample store into said test sample receiver by said transfer mechanism, said cooling or heating device effects the cooling or heating of said test and reference samples to carry out said measurement, and thereafter said test sample is removed from said test sample receiver by said transfer mechanism after said measurement.

2. Apparatus as claimed in claim 1, wherein said coupler curve also extends substantially rectilinearly over said test sample receiver and said reference sample receiver.

3. Apparatus as claimed in claim 1 wherein said lifting mechanism includes:
   a suction member vertically movable between a lowered and a raised position, said suction member being connected to a vacuum source and adapted to engage one of said encapsulated test samples in its lowered position;
   a pneumatic lifting mechanism for moving said suction member between said lowered and said raised position; and
   a plurality of valves controlled by said program control device, said valves being arranged to supply a vacuum to said suction member and pressurized gas to said pneumatic lifting mechanism.

4. Apparatus as claimed in claim 3, wherein each said encapsulated test samples includes, on the top surface thereof, a cup-shaped recess with a flat ground and a rim extending outwards in funnel-shaped manner.

5. Apparatus as claimed in claim 3, wherein said suction member is adapted to receive a pressure pulse for releasing said encapsulated test sample.

6. Apparatus as claimed in claim 3, wherein a pressure sensor responsive to vacuum is connected to said suction member, the signal of said pressure sensor being applied to said program control device as a feedback of the function.

7. Apparatus as claimed in claim 1, wherein:
   each said encapsulated test sample at said test sample receiver can be covered by a cover;
   a place of deposit for said cover; and
   said transfer mechanism is program controlled by said program control device so that during each measuring cycle, said cover is transferred from said place of deposit and placed on said test sample receiver prior to said measurement and after a test sample has been transferred into said test sample receiver; said cover is removed from said test sample receiver and deposited on said place of deposit after said measurement but before said test sample is removed from said test sample receiver.

8. Apparatus as claimed in claim 1, further comprising means for covering said test sample receiver and said reference sample receiver by a cover plate, said plate being movable between an open and a closed position by a pneumatic cylinder controlled by said program control device.

9. Apparatus as claimed in claim 8, wherein:
   said cover plate in its closed position is in sealing engagement with a base around said test sample receiver ans said reference sample receiver, thus forming a sealed space enclosed by said cover plate within the zone of sealing engagement between the cover plate and base;
   means for providing pressurized gas to the space so formed; and
   a pressure sensor adapted to sense the pressure in said space, said sensor providing a signal which is applied to said program control device as a feedback of the position of said cover plate.

10. Apparatus for examination of heats of transformation of material samples, comprising:
    a test sample receiver for one of a plurality of individually encapsulated test samples;
    a reference sample receiver for a reference sample;
    a test sample store for receiving said plurality of individually encapsulated test samples;
    a program-controlled transfer mechanism by which one of said plurality of test samples can be transferred from said test sample store into, and removed from, said test sample receiver;

a housing filled with inert gas enclosing said test and reference sample receivers, test sample store and transfer mechanism and having a lock through which test samples can be inserted into said test sample store;

a program controlled cooling or heating device for the controlled cooling or heating of said test and reference samples;

a measuring device responsive to differences in the heating-up characteristic of said test and reference samples; and a program control means for controlling said cooling or heating device and said transfer mechanism whereby during one measurement cycle such a test sample is transferred from said test sample store into said test sample receiver by said transfer mechanism, said cooling or heating device effecting cooling or heating of said test and reference samples to carry out said measurement, and thereafter effecting removal of said test sample from said test sample receiver by said transfer mechanism following said measurement.

11. Apparatus as claimed in claim 10, wherein:

each said encapsulated test sample at said test sample receiver can be covered by a cover;

a place of deposit for said cover; and said transfer mechanism is program-controlled by said program control device so that during each measuring cycle, said cover is transferred from said place of deposit and placed on said test sample receiver prior to said measurement and after a test sample has been transferred into said test sample receiver; said cover is removed from said test sample receiver and deposited on said place of deposit after said measurement but before said test sample is removed from said test sample.

12. Apparatus as claimed in claim 10, further comprising means for covering said test sample receiver and said reference sample receiver by a cover plate, said plate being movable between an open and a closed position by a pneumatic cylinder controlled by said program control device.

13. Apparatus as claimed in claim 12, wherein:

said cover plate in its closed position is in sealing engagement with a base around said test sample receiver and said reference sample receiver, thus forming a sealed space enclosed by said cover plate within the zone of sealing engagement between the cover plate and base;

means for providing pressurized gas to the space so formed; and a pressure sensor adapted to sense the pressure in said space, said sensor providing a signal which is applied to said program control device as a feedback of the position of said cover plate.

* * * * *

UNITED STATES PATENT OFFICE
CERTIFICATE OF CORRECTION

Patent No. 4,874,250  Dated Oct. 17, 1989

Inventor(s) Winfried Gonner

It is certified that error appears in the above-identified patent and that said Letters Patent is hereby corrected as shown below:

On the title page:

In paragraph (73) the name of Assignee

"The Perkin-Elmer Corporation, Norwalk, Conn."

should read:

--Bodenseewerk Perkin-Elmer & Co., GmbH, Überlingen, Federal Republic of Germany--

Signed and Sealed this

Twentieth Day of November, 1990

Attest:

HARRY F. MANBECK, JR.

Attesting Officer

Commissioner of Patents and Trademarks